United States Patent [19]

VandenBerg

[11] Patent Number: Plant 6,312

[45] Date of Patent: Sep. 27, 1988

[54] CHRYSANTHEMUM PLANT NAMED NEOGA

[75] Inventor: Cornelis P. VandenBerg, Salinas, Calif.

[73] Assignee: Yoder Brothers, Inc., Barberton, Ohio

[21] Appl. No.: 920,270

[22] Filed: Oct. 17, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Neoga particularly characterized by its flat capitulum form; spoon daisy capitulum type; purple ray floret color; diameter across face of capitulum of up to 12 cm at maturity when grown as a pinched disbudded pot mum; uniform eight week photoperiodic flowering response to short days; medium plant height when grown as a pinched pot mum; its recommended use both as disbudded and spray pot mums, and by its spreading and prolific branching pattern.

3 Drawing Sheets

The present invention comprises a new and distinct cultivar of Chrysanthemum, botanically known as *Chrysanthemum morifolium*, and referred to by the cultivar name Neoga.

Neoga, identified as 82350005, was originated from a cross made by me in a controlled breeding program in Salinas, Calif., in 1982.

The female parent of Neoga was an unnamed seedling identified as 81C48005. The male parent of Neoga was an unnamed seedling identified as 81862002.

Neoga was discovered and selected as one flowering plant within the progeny of the stated cross by Cornelis P. VandenBerg in December of 1982, in a controlled environment in Salinas, Calif.

The first act of asexual reproduction of Neoga was accomplished when vegetative cuttings were taken from the initial selection in March of 1983 in a controlled environment in Salinas, Calif., by technicians working under formulations established and supervised by Cornelis P. VandenBerg.

Horticultural examination of controlled flowerings of successive generations of plantings has shown that the unique combination of characteristics as herein disclosed for Neoga are firmly fixed and are retained through successive generations of asexual reproduction.

Neoga has not been observed under all possible environmental conditions. The phenotype may vary significantly with variations in environment such as temperature, light intensity, and day length.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Neoga, which, in combination, distinguish this Chrysanthemum as a new and distinct cultivar:

1. Flat capitulum form.
2. Spoon daisy capitulum type.
3. Purple ray floret color.
4. Diameter across face of capitulum up to 12 cm at maturity when grown as a pinched disbudded pot mum.
5. Uniform eight week photoperiodic flowering response to short days.

6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Recommended both as disbudded and spray pot mum.
8. Branching pattern is spreading and prolific.

The accompanying photographic drawings show typical inflorescence and leaf characteristics of Neoga, with the colors being as nearly true as possible with illustrations of this type.

Sheet 1 is a color photograph of Neoga grown as a pinched disbudded pot mum.

Sheet 2 is a black and white photograph of three views of the inflorescence of Neoga.

Sheet 3 is a black and white photograph showing the upper and under sides of the leaves of Neoga at three stages of development (mature, intermediate and immature).

Of the commercial cultivars known to the inventor, the most similar in comparison to Neoga is Spears, disclosed in U.S. Plant Pat. No. 5,620. Reference is made to attached Chart A, which compares certain characteristics of Neoga to the same characteristics of Spears.

Similar traits are capitulum type and form, branching pattern, plant height and flowering response. Neoga has a purple ray floret color, Spears has a white ray floret color. Neoga has a larger capitulum diameter than Spears, and is recommended both as disbudded and spray mum, while Spears is recommended as spray mum only.

In the following description, color references are made to The Royal Horticultural Society Colour Chart. The color values were determined from plant material grown as a pinched disbudded pot mum in Salinas, Calif. on Mar. 20, 1986.

Classification:

*Botanical.*—*Chrysanthemum morifolium*, Ramat., cv. Neoga.

*Commercial.*—Spoon daisy disbudded and spray pot mum.

INFLORESCENCE

A. Capitulum:
*Form.*—Flat.
*Type.*—Spoon daisy.
*Diameter across face.*—Up to 12 cm at maturity.

B. Corolla of ray florets:
*Color (general tonality from a distance of three meters).*—Purple.
*Color (upper surface, spoon tips).*—Streaked 78C to 78D. Under high light conditions upper surface of spoon tips fades to almost white.
*Color (under surface, tubes).*—78B to 78C.
*Shape.*—Base tubular. Distal portion open, flattened and spoon like.

C. Corolla of disc florets:
*Color (mature).*—2A to 2B.
*Color (immature).*—144B to 144C.

D. Reproductive organs:
*Androecium.*—Present in disc florets only; no pollen.
*Gynoecium.*—Present in both ray and disc florets.

PLANT

A. General appearance:
*Height.*—Medium; 25 to 35 cm as a pinched pot mum with 0 to 7 long days after pinch prior to short days and 1 application of 2500 ppm B-9 SP.
*Branching pattern.*—Spreading and prolific.

B. Foliage:
*Color (upper surface).*—137A to 137B.
*Color (under surface).*—147B.
*Shape.*—Deeply lobed and serrated.

CHART A

COMPARISON OF NEOGA AND SPEARS

| CULTIVAR | RAY FLORET COLOR | CAPITULUM FORM & TYPE | BRANCHING PATTERN |
|---|---|---|---|
| NEOGA | PURPLE | SPOON DAISY | SPREADING |
| SPEARS | WHITE | SPOON DAISY | SPREADING |

| CULTIVAR | DIAMETER ACROSS FACE OF CAPITULUM | PLANT HEIGHT | FLOWERING RESPONSE PERIOD | RECOMMENDED USE |
|---|---|---|---|---|
| NEOGA | up to 12 cm AS DISBUDDED POT MUM | MEDIUM | 8 WEEK | DISBUD and SPRAY |
| SPEARS | 7 to 8 cm AS SPRAY POT MUM | MEDIUM | 8 WEEK | SPRAY only |

COMPARISONS MADE OF PLANTS GROWN AS PINCHED POT MUM IN SALINAS, CALIFORNIA

I claim:

1. A new and distinct Chrysanthemum plant named Neoga, as described and illustrated, and particularly characterized as to uniqueness by the combined characteristics of flat capitulum form; spoon daisy capitulum type; purple ray floret color; diameter across face of capitulum of up to 12 cm at maturity when grown as a pinched disbudded pot mum; uniform eight week photoperiodic flowering response to short days; medium plant height when grown as a pinched pot mum; its recommended use both as disbudded and spray pot mums, and by its spreading and prolific branching pattern.

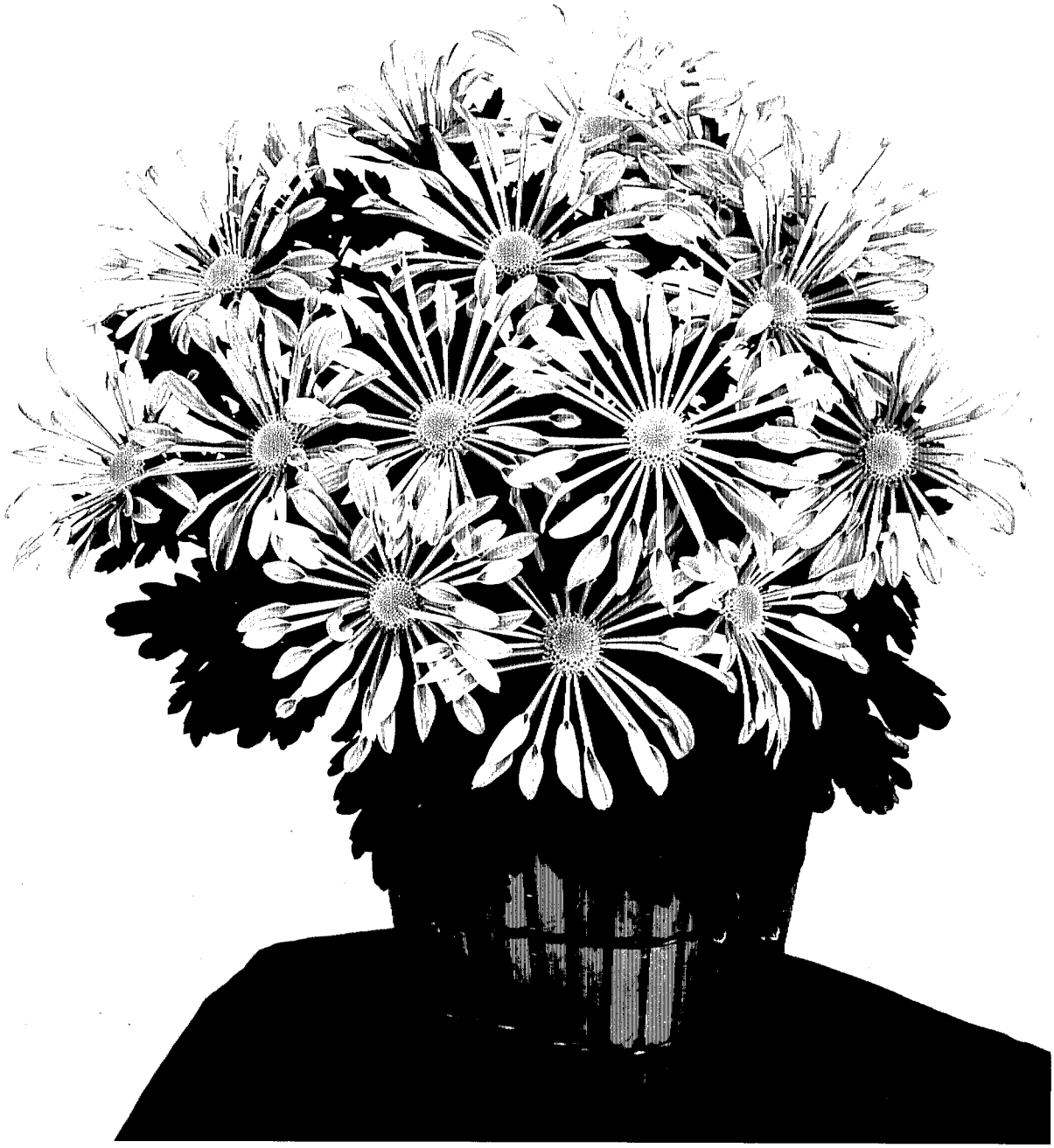

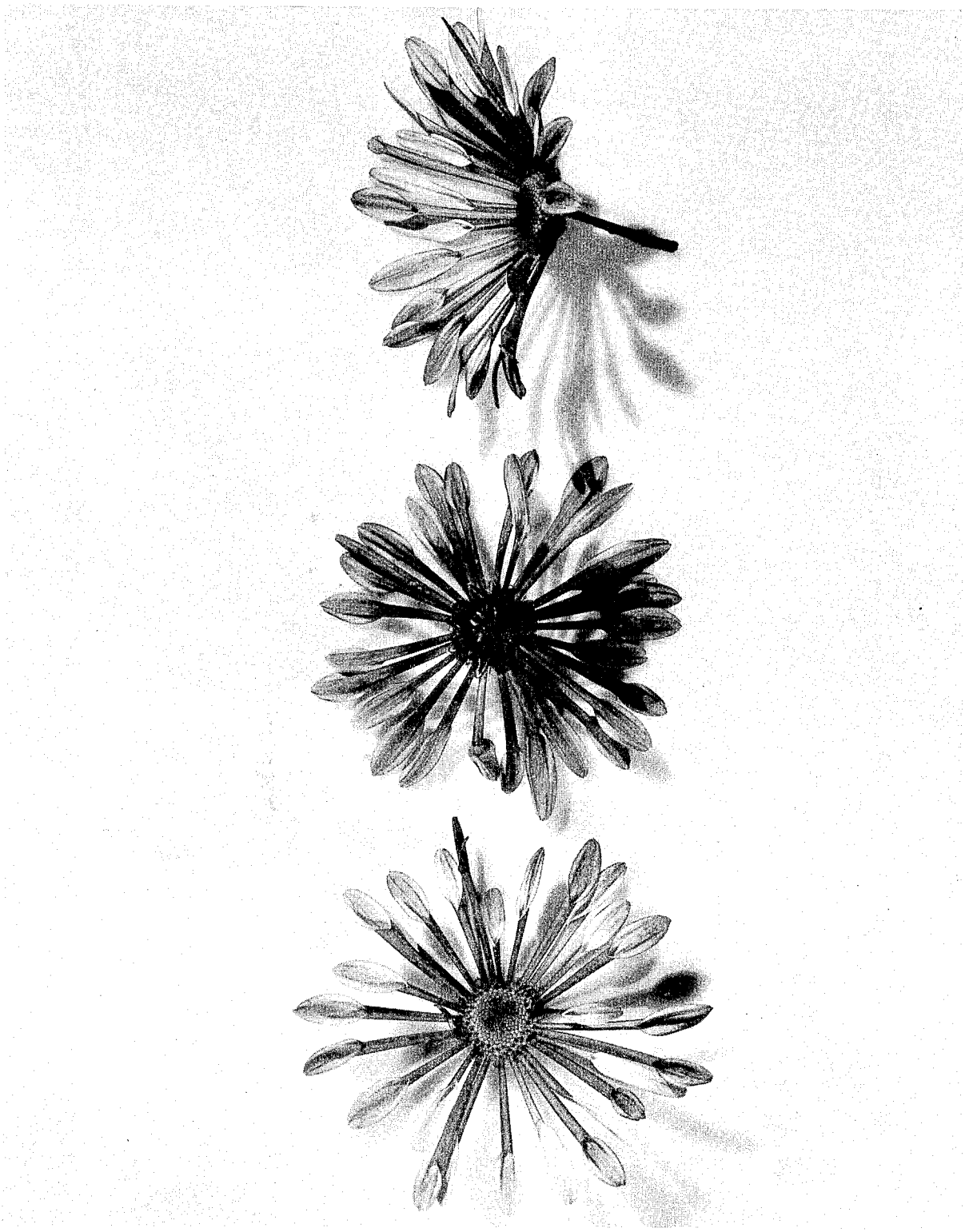

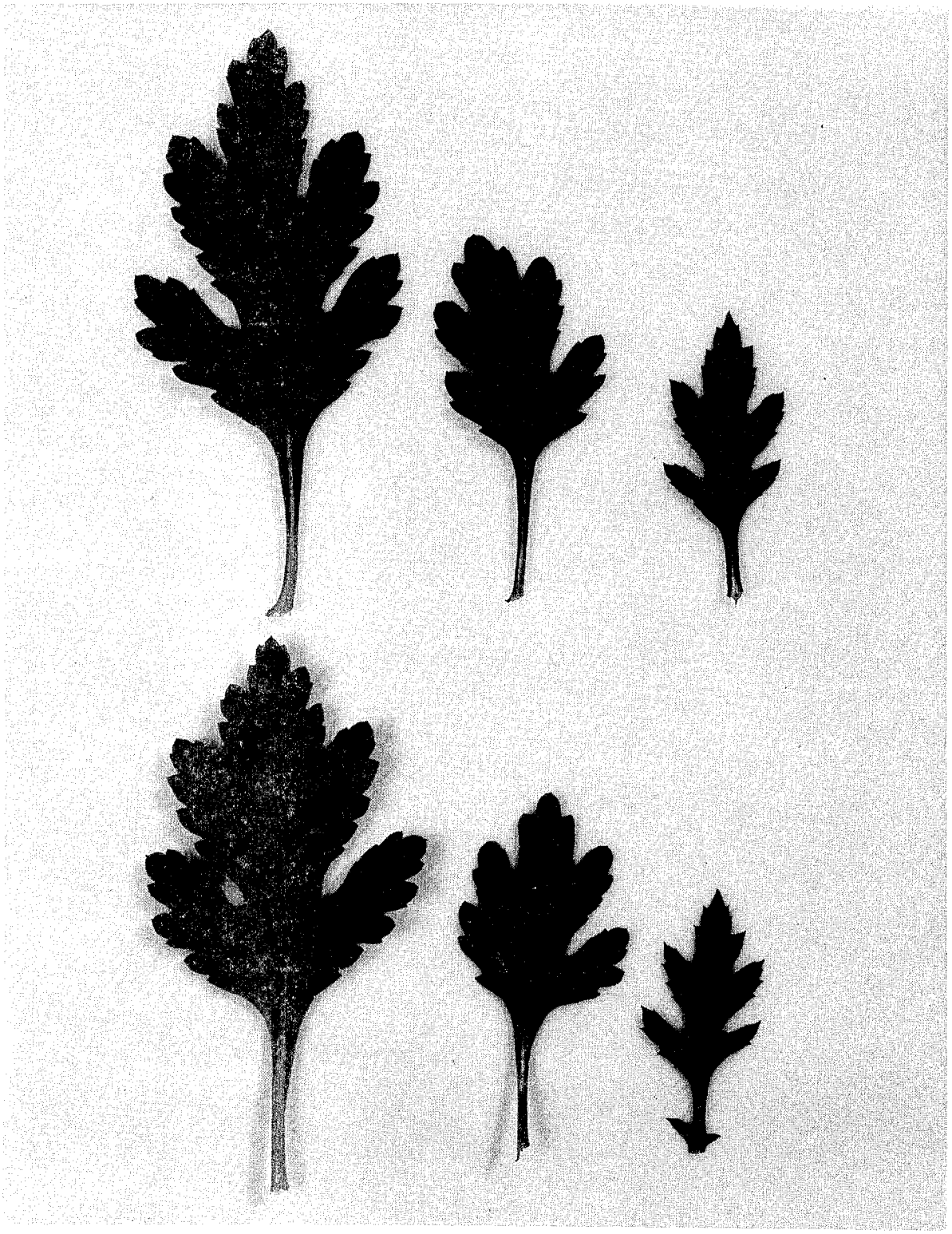

* * * * *